United States Patent [19]
Hoeprich, Jr.

[11] Patent Number: 5,869,603
[45] Date of Patent: Feb. 9, 1999

[54] PEPTIDES REPRESENTING EPTIOPIC SITES ON R-IFN-β, ANTIBODIES THERETO, AND USES THEREOF

[75] Inventor: Paul D. Hoeprich, Jr., Alameda, Calif.

[73] Assignee: Schering Aktiengesellschaft, Germany

[21] Appl. No.: 807,030

[22] Filed: Dec. 12, 1991

Related U.S. Application Data

[63] Continuation of Ser. No. 257,651, Oct. 14, 1988, abandoned.

[51] Int. Cl.$^6$ .............................. C07K 7/00; A61K 38/19
[52] U.S. Cl. .............................. 530/328; 514/15; 514/16; 424/85.6
[58] Field of Search .............................. 530/351, 388.23, 530/328; 424/85.6; 514/16

[56] References Cited

U.S. PATENT DOCUMENTS 4,311,639  1/1982  Ganfield et al. .

FOREIGN PATENT DOCUMENTS 0 163 993  5/1985  European Pat. Off. .

OTHER PUBLICATIONS

Redlich et al *PNAS* 88:4040–4044 (1991).
Kawade et al. *Immunology* 56:489 (1985).
Redlich et al. *Eur J. Immunology* 20:1933–1939 (1990).
Wang et al *Hybridoma* 3(4) 321–332 (1984).
Chow et al. (1984) "Antibodies to Synthetic Peptides of Human Interferon–: Use in Biosynthetic Studies" *J. Biol. Chem.* 259:12220–12225.
Geysen et al. (1984) "Use of peptide synthesis to probe viral antigens for epitopes to a resolution of a single amino acid" *Proc. Nat'l Acad. Sci. USA* 81:3998–4002.
Geysen et al. (1987) "Strategies for epitope analysis using peptide synthesis" *J. Immunological Methods* 102:259–274.
Rashidbaigi et al. (1987) "Interferons: Protein Structure" in Baren et al. (eds) *The Interferon System: A Current Review to 1987*, Chapter 15, pp. 149–168.
May et al. (1987) "Structure, Genetics and Function of Human 2–Interferon" *J. Leukocyte Biology*; and Seghal et al. (1987) Structure, Genetics and Function of Human 2 Interferon in Cantell and Schellekens (eds.) *The Biology of the Interferon System 1986: Proceedings of the 1986 ISIR–TNO meeting on the interferon system, 7–12 Sep. 1986, Dipoli Congress Center, Espoo, Finland*, Martinus Nijhoff Publishers, Dordrecht, pp. 25–30.
Stewart et al. (1987) "Chemical Mutagenesis of Human Interferon–: Construction, Expression in *E. coli*, and Biological Activity of Sodium Bisulfite–Induced Mutations" *DNA* 6:119–128.
Thompson et al. (1986) "Monoclonal Antibodies to Human–Interferon Produced by Adoptive Transfer in Irradiated Mice" *J. Interferon Res.* 6:59–65.

*Primary Examiner*—Frank C. Eisenschenk
*Attorney, Agent, or Firm*—Millen, White, Zelano & Branigan, P.C.

[57] ABSTRACT

The present invention discloses synthetic peptides and antibodies raised thereto wherein the synthetic peptides represent important epitopic sites recognized by monoclonal antibodies which can neutralize IFN-β. Also, the uses of these peptides or antibodies thereto as diagnostics and therapeutics are disclosed.

20 Claims, 4 Drawing Sheets

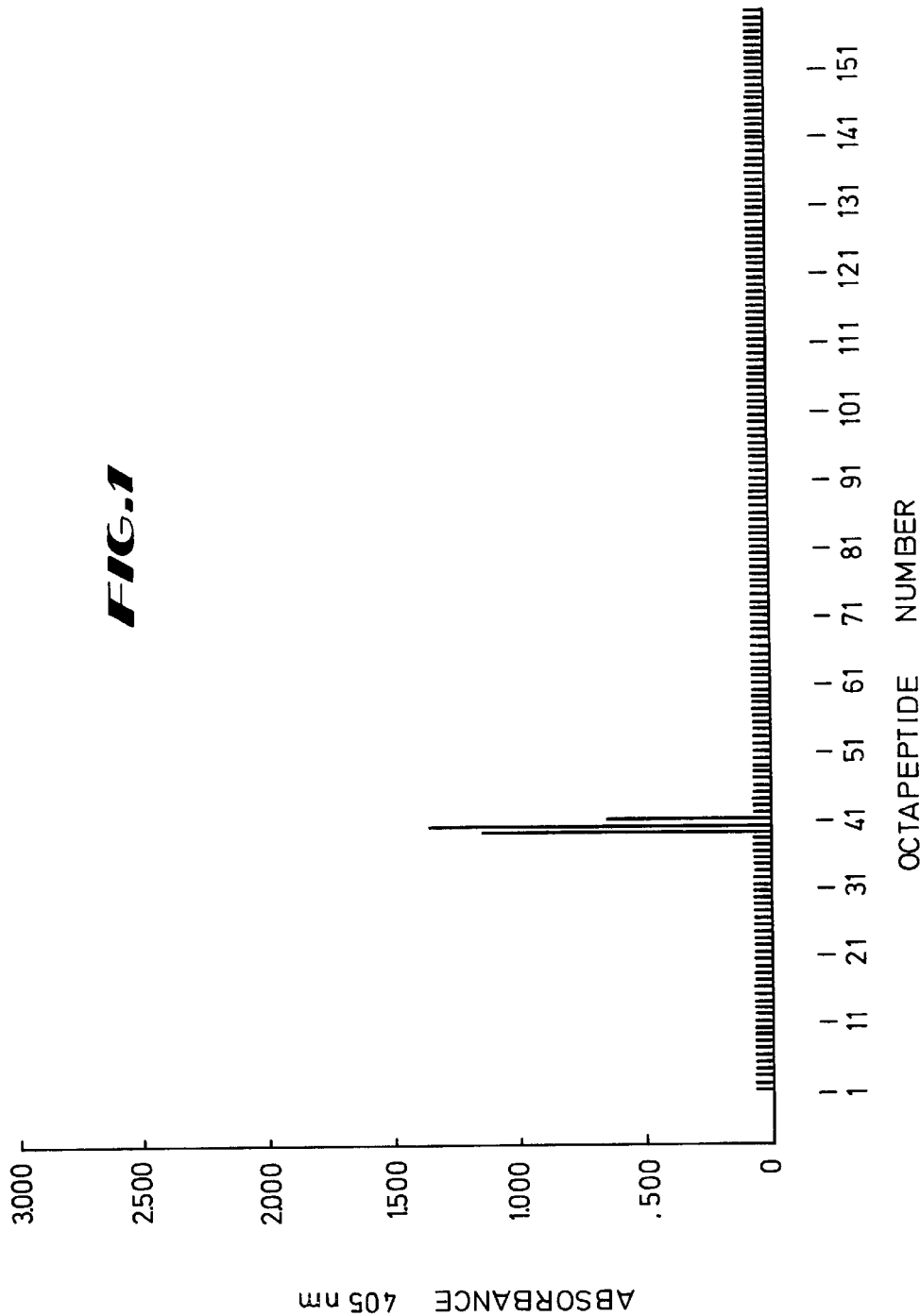

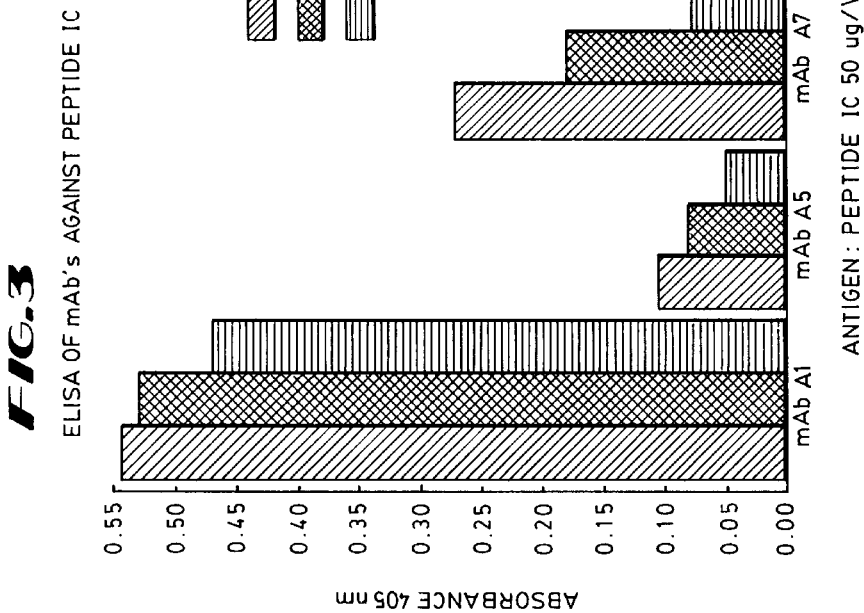
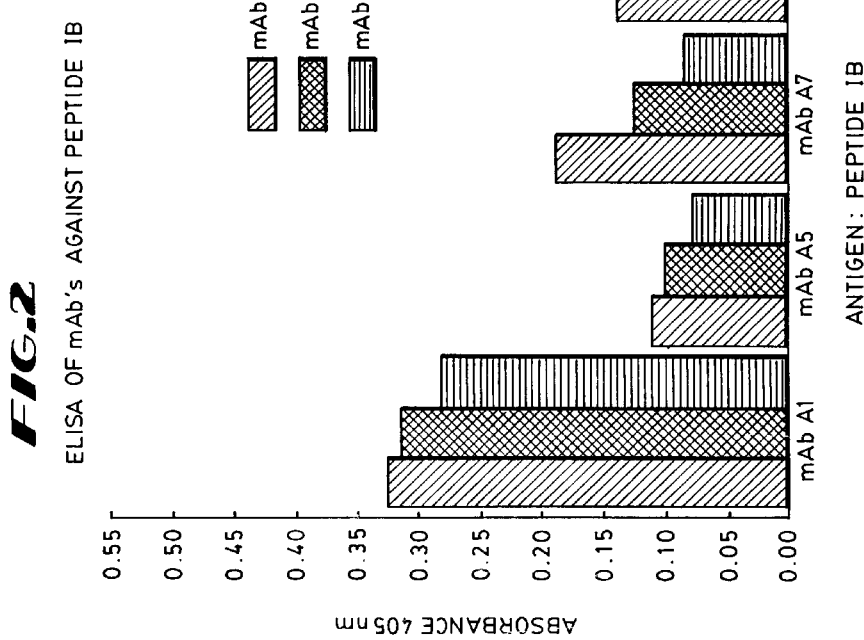

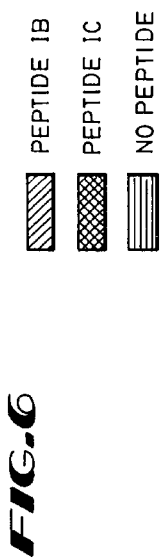

PEPTIDES REPRESENTING EPTIOPIC SITES ON R-IFN-β, ANTIBODIES THERETO, AND USES THEREOF

This application is a continuation of application Ser. No. 07/257,651, filed on Oct. 14, 1988, now abandoned.

BACKGROUND OF THE INVENTION

Human interferons (IFN's) are members of a biologically potent family of cytokines. Known activities of these proteins include those which are antiviral, antiproliferative and immunomodulatory. Three antigenically distinct types of interferons are known: α(leukocyte), β(fibroblast) and γ(immune). They all bind to high affinity cell surface receptors; IFNA and IFN-β share a receptor that is distinct from the one bound by IFNγ. The events responsible for biological activity beyond receptor binding are poorly understood. Recent studies, however, showing IFN's efficacy in treating certain viral diseases and cancer have been encouraging. These clinical observations have stimulated interest in further understanding the molecular basis of activity. To this end, study of genetically engineered IFN's has provided insight to structure-function relationships. An altered form of fibroblast interferon, rIFN-$β_{ser}$, is one such protein. It is a recombinant molecule the sequence of which is based on human fibroblast interferon. In this protein, a cysteine residue at position 17 was replaced with serine by site-directed mutagenesis. The resulting molecule is fully active having the same biologic activities as natural IFN-β and it is now a clinically useful protein therapeutic. In this disclosure IFN-β will be used to denote both natural and recombinant forms of IFN-β, but rIFN-β is sometimes used to indicate the recombinant form of IFN-β when that more clearly describes the work presented. In clinical usage it has been found that some patients produce antibodies to IFN-β which neutralize its biologic activity. In other words these antibodies have the ability to inhibit all or some of the beneficial activities of IFN-β. The present invention is concerned with the discovery of peptides that represent the sites to which neutralizing antibodies bind to IFN-β. These peptides may be the same epitopes responsible for the biologic activity of IFN-β. The peptides of this invention may be useful in inhibiting the neutralizing effect of neutralizing antibodies to IFN-β. They also have diagnostic applications for the detection of neutralizing antibodies. Antibodies raised to or having specific binding affinity for the peptides mentioned above are also a part of this invention as they can be used to detect and monitor levels of IFN-β in patients during the course of treatment.

SUMMARY OF THE INVENTION

The present invention discloses synthetic peptides which represent epitopic sites on both natural and recombinant human IFN-β(HuIFN-β). In one aspect of the invention, the epitopic peptides represent the site(s) where neutralizing antibodies bind to IFN-β thereby reducing or eliminating its activity. Another aspect of this invention provides a diagnostic or prognostic assay whereby a patient receiving IFN-β therapy can be assessed for production of IFN-β neutralizing antibodies. A third aspect of this invention provides a method for treating a patient to reduce or eliminate the effect of neutralizing antibodies during IFN-β therapy. A fourth aspect of this invention provides a method for detecting IFN-β levels in a sample. The peptides of this invention may also represent the epitopes responsible for IFN-β's biological activity.

BRIEF DESCRIPTION OF THE DRAWINGS

FIG. 1 is a plot of the absorbance obtained in an antibody-binding ELISA when a neutralizing mAb, A1 in this example, is allowed to react with the set of sequentially overlapping synthetic octapeptides that span the sequence of rIFN-β, i.e. peptide 1 contains residues 1–8, peptide 2 residues 2–9, etc. to peptide 157 containing residues 157–164.

FIGS. 2, 3, 4 and 5 illustrate binding of neutralizing and non-neutralizing mAb's to peptides IB, IC, IE and a control peptide respectively.

FIG. 6 represents inhibition of mAb binding to IFN-β in the presence of peptides IB, IC and a control peptide.

FIG. 7 illustrates binding to IFN-β of rabbit polyclonal antibodies raised against synthetic peptides IB and IC to IFN-β.

DESCRIPTION OF THE PREFERRED EMBODIMENT

Figure 5:
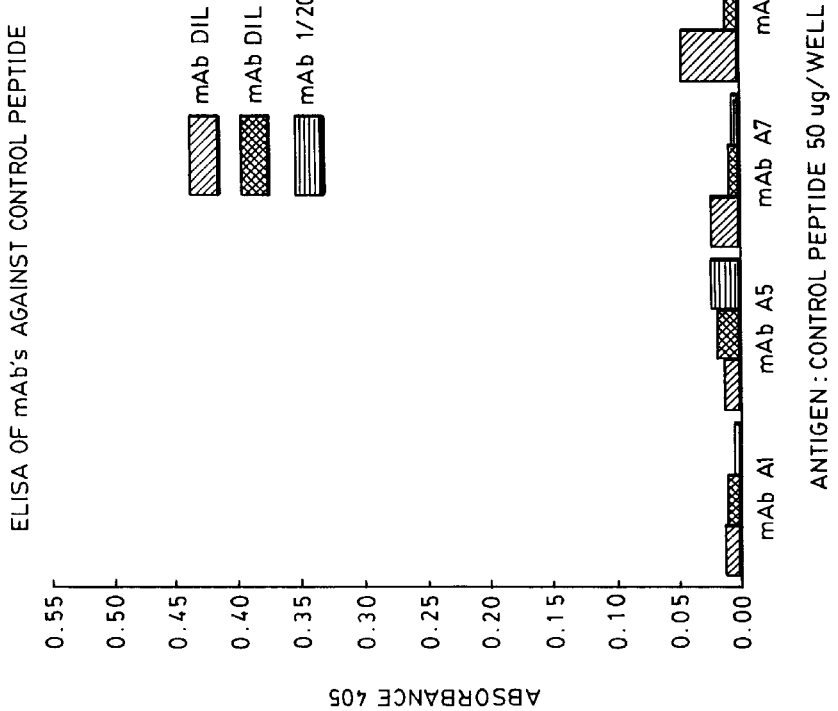
Figure 4:
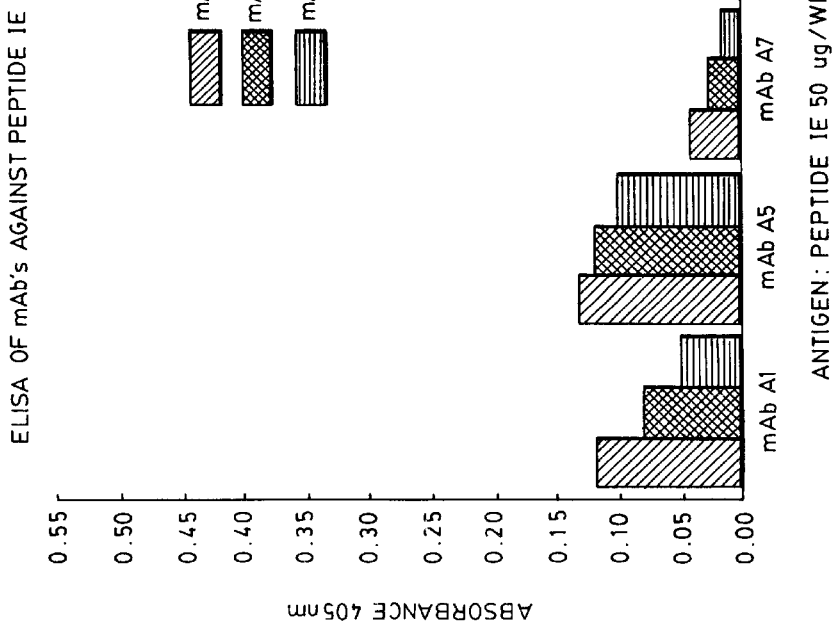

During IFN-β treatment it Is known that some patients develop neutralizing antibodies to this cytokine potentially reducing its efficacy as a treatment for viral and proliferative diseases. The present invention discloses peptides which have the ability to interfere with mab's that neutralize the activity of IFN-β. These antibodies have been produced against rIFN-β and were screened for their ability to neutralize biologic functions commonly associated with this cytokine. The present invention identifies the specific epitope or epitopes to which mAb's that neutralize IFN-β activity bind. These epitopes were discovered using the Geysen method of epitope mapping which involves multiple peptide synthesis on activated polyethylene rods (Geysen, H. M., Meloen, R. H., and Barteling, S. J. [1984] *Proc. Natl. Acad. Sci USA* 81, 3998–4002). The Geysen method provides for simultaneous synthesis of hundreds of peptides which can then be assayed for antibody binding. Based on the amino acid sequence of rIFN-β, 157 octapeptides were synthesized in duplicate by moving one amino acid at a time through the entire sequence of rIFN-β. The peptides synthesized were then reacted with the neutralizing mAb's to determine binding between them. A typical result is shown in FIG. 1. The first class of peptides of this invention are selected from the following sequence:

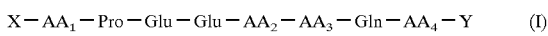

where X is $NH_2$ or an amino acid sequence up to 10 amino acids long, selected in sequence from the following sequence:

Tyr-Cys-Leu-Lys-Asp-Arg-Met-Asn-Phe-Asp-;

Y is COOH or an amino acid sequence up to 13 amino acids long, selected in sequence from the following sequence:

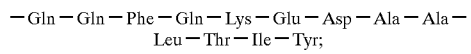

$AA_1$ is Ile, Phe, Leu, Val, Arg, Tyr, or NorLeu, $AA_2$ is Ile, Leu, Arg, Val, or NorLeu;

$AA_3$ is Lys, Ile, Leu, Arg, Val, or NorLeu;

$AA_4$ is Leu, Phe, Tyr, Ile, Val, Arg, or Met.

More preferably:

$AA_1$ is Ile, Phe, or Leu;

$AA_2$ is Ile, Leu, or Arg;

$AA_3$ is Lys, Ile, or Leu; and $AA_4$ is Leu, Phe, or Tyr.

More preferably the peptides of this invention are one of the following sequences:

$$X—Ile—Pro—Glu—Glu—Ile—Lys—Gln—Leu—Y \quad (IA)$$

where X and Y are defined the same as for formula I above.

Most preferably the peptides are one of the following sequences:

$$\begin{aligned}&\text{Leu—Lys—Asp—Arg—Met—Asn—Phe—Asp—Ile—}\\&\text{Pro—Glu—Glu—Ile—Lys—Gln—Leu}\end{aligned} \quad (IB)$$

$$\begin{aligned}&\text{Ile—Pro—Glu—Glu—Ile—Lys—Gln—Leu—Gln—Gln—}\\&\text{Phe—Gln—Lys—Glu—Asp—Ala—Ala}\end{aligned} \quad (IC)$$

$$\begin{aligned}&\text{Leu—Lys—Asp—Arg—Met—Asn—Phe—Asp—Ile—}\\&\text{Pro—Glu—Glu—Ile—Lys—Gln—Leu—Gln—Gln—}\\&\text{Phe—Gln—Lys—Glu—Asp—Ala—Ala}\end{aligned} \quad (ID)$$

$$NH_2—Ile—Pro—Glu—Glu—Ile—Lys—Gln—Leu—COOH \quad (IE)$$

Most preferably the peptides of this invention are those found between residues 30–60 of rIFN-β and having at least the sequence of any of formulas I–IE above. Depending on the end use of the peptides of this invention, e.g. to enhance solubility or stabilize a conformation, it may be necessary to modify the peptides by means known in the art of peptide chemistry. Also, longer peptides are contemplated as part of this invention by adding additional amino acids from the rIFN-β sequence. Another aspect of this invention is the antibodies raised to or having binding affinity for the peptides of formulas I–ID above.

The peptides of the present invention can be prepared by conventional processes for synthesizing peptides; more specifically, using processes as described in Schroder and Lubke, *The Peptides,* Vol. 1, published by Academic Press, New York (1966), or Izumiya, et al., *Synthesis of Peptides,* published by Maruzen Publishing Co., Ltd., (1975), both of which are herein incorporated by reference. For example, an azide process, an acid chloride process, a symmetric anhydride process, a mixed anhydride process, a DCC process, an active ester process (for example: p-nitrophenyl ester, N-hydroxysuccinimide ester, or cyanomethyl ester), a carbodiimidazole process, an oxidative-reductive process, or a DCC/additive process can be used. Solid phase and solution phase syntheses are both applicable to the foregoing processes.

The peptides of the present invention are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. (Amino groups that are not being used in the coupling reaction must be protected to prevent coupling at an incorrect location.)

In the case where a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins of polystyrene, such as chloromethyl resin or bromomethyl resin; hydroxymethyl resins, phenol resins, tert-alkyloxycarbonyl-hydrazidated resins, and the like.

An amino group-protected amino acid is bound in sequence through condensation of its reactive carboxyl group to the terminal amino group of the growing chain. After synthesizing the complete sequence, the peptide is removed from the insoluble carrier to yield free the peptide. This solid-phase approach is generally described by Merrifield, et al. in *J. Am. Chem. Soc.,* 85, 2149–2156 (1963), which is herein incorporated by reference.

In the foregoing process, it is preferred that respective amino acids of histidine, tyrosine, glutamic acid, lysine, serine, cysteine, threonine, and aspartic acid be protected at the side chain functional groups. These side chain functional groups are protected with ordinary protective groups which are removed after completion of the final reaction.

Examples of protective groups for imidazole moiety include:

benzyloxycarbonyl, Boc, tert-amyloxycarbonyl, isobornyloxycarbonyl, p-methoxybenzyloxycarbonyl, Cl-Z, adamantyloxycarbonyl, trifluoroacetyl, phthalyl, formyl, o-nitrophenylsulfenyl, diphenylphosphinothioyl, and the like.

Examples of protective groups for the imino group of histidine include: Tos, Bzl, DNP, trityl, and the like.

Examples of protective groups for the hydroxy group of tyrosine include: Bzl, Cl$_2$-Bzl, BrZ, benzyloxycarbonyl, acetyl, Tos, and the like.

Examples of protective groups for the amino group of lysine include: benzyloxycarbonyl, Cl-Z, Cl$_2$-Bzl Boc, Tos, and the like.

Protection for the carboxyl groups of glutamic acid and aspartic acid includes: esterification of the carboxylic acids with benzyl alcohol, methanol, ethanol, tert-butanol, and the like.

Examples of protective groups for the hydroxy of serine include: O-benzyl, O-tert-butyl, and the like.

Examples of protective groups for threonine include: O-benzyl, O-tert-butyl, and the like.

Examples of protective groups for cysteine include: paramethoxybenzyl, acetamideomethyl, S-trityl, S-butyl, and the like.

Examples of activated carboxyl groups include: the corresponding acid chlorides, symmetric anhydrides, mixed anhydrides, azides, and active esters (esters with pentachlorophenol, p-nitrophenol, N-hydroxysuccinimide, N-hydroxybenzotriazole, N-hydroxy-5-norbornene-2,3-dicarboxydiimide, and the like).

The peptides of this invention can also be prepared through DNA techniques. The amino acid sequence of the desired peptide is used to deduce the codon sequence for the single-stranded DNA, synthesized using conventional synthetic techniques (including multiple gene copy techniques), then the double-stranded DNA is prepared and inserted at a suitable site in a cloning vehicle, vector, or plasmid. An appropriate organism, such as bacterial cells, yeast cells, or mammalian cells, is transformed to obtain expression of the desired peptide.

The prepared peptides of the present invention can be isolated and purified from the reaction mixture by means of peptide separation, for example, by extraction, countercurrent distribution, column chromatography, high performance liquid chromatography, and the like.

The peptides of this invention form salts with a variety of inorganic or organic bases. The non-toxic, pharmaceutically-acceptable salts are preferred, although other salts are also useful in isolating or purifying the product. Such pharmaceutically-acceptable salts include metal salts, such as sodium, potassium, or lithium, alkaline earth metal salts, such as calcium or magnesium, and salts derived from amino acids, such as arginine or lysine. The salts are obtained by reacting the acid form of the peptide with a molar equivalent of the base supplying the desired ion in a medium in which the salt precipitates or in aqueous medium and then lyophilizing.

Similarly, the peptides form salts with a variety of inorganic and organic acids. Again, the non-toxic, pharmaceutically-acceptable salts are preferred, although other salts are also useful in isolating or purifying the product. Such pharmaceutically-acceptable salts include those formed with hydrochloric acid, methanesulfonic acid, sulfuric acid, maleic acid, acetic acid, palmitic acid, and the like. The salts are obtained by reacting the product with a molar equivalent amount of the acid in a medium in which the salt precipitates.

As noted above, the present invention also embraces antibodies. For example, antibodies or antibody fragments, e.g., F(ab')$_2$ or Fab fragments, having binding affinity for the peptides of formulas I–ID may be useful in immunoassays to detect levels of rIFN-β in bodily fluids of patients receiving the protein therapeutically. Accordingly, to facilitate the production of antibodies according to the invention the peptides of the invention are preferably treated or prepared in a fashion which optimizes their antigenicity.

Antigenic peptides can be prepared by using the peptides or fragments of the peptides of the present invention as haptens and reacting the peptides or fragments with a suitable carrier in the presence of a hapten-carrier binding agent. In this case, natural and synthetic proteins having a high molecular weight, which are conventionally employed in the preparation of antigens, can be employed as carriers to be bound to the haptens. Examples of such carriers include: albumins of animal sera, globulins of animal sera, thyroglobulins of animals, hemoglobulins of animals, hemocyanins of animals, such as Keyhole limpet hemocyanin (KLH), proteins extracted from ascaris, polylysine, polyglutamic acid, lysine-glutamic acid copolymers, and copolymers containing lysine or ornithine.

As hapten-carrier binding agents, those conventionally employed in the preparation of antigens can be employed. Specific examples of these agents include: diazonium compounds for cross linking aromatic residues, aliphatic dialdehydes for cross linking an amino group with an amino group, dimaleimide compounds for cross linking a thiol group with a thiol group, maleimido-N-hydroxysuccinimide esters for cross linking an amino group with a thiol group, and agents used in conventional peptide bond forming reactions in which amide bonds are formed from an amino group and a carboxyl group. Also as the hapten-carrier binding agent, it is possible to use diazonium aryl carboxylic acids, such as p-diazonium phenylacetic acid, in combination with conventional peptide bond-forming agents, such as the dehydrating and condensing agents described above.

The coupling reaction for preparing the antigenic forms of the peptides of the present invention is suitably carried out in an aqueous solution or a conventional buffer solution having a pH of 7 to 10, preferably in a buffer solution having a pH of 7.5 to 9, at temperatures ranging from about o to 400C, preferably around room temperature.

The coupling reaction is generally completed within about 1 to about 24 hours, preferably 3 to 5 hours. Representative examples of buffer solutions which can be used in the above process include:

0.2N sodium hydroxide-0.2M boric acid-0.2M potassium chloride buffer solution;

0.2M sodium carbonate-0.2M boric acid-0.2M potassium chloride buffer solution;

0.05M sodium tetraborate-0.2M boric acid-0.05M sodium chloride buffer solution; and 0.1M dihydrogen potassium phosphate-0.05M sodium tetraborate buffer solution.

Proportions of the hapten, hapten-carrier binding agent, and carrier can be appropriately determined, but it is preferred that the molar ratio of hapten to carrier be about 20 to about 1 and the molar ratio of binding agent to hapten be about 10 to about 1. In the coupling reaction, the hapten is bound to the carrier via the hapten-carrier binding agent to obtain a desired antigen composed of a peptide-carrier complex.

After completion of the coupling reaction, the antigen can be isolated and purified by means of dialysis, gel filtration, fractional precipitation, and the like.

The antibody or antibodies of the present invention which exhibit binding affinity for a peptide or peptides of this invention, can be monoclonal or polyclonal, but monoclonal is preferred. In general, antibodies may be obtained by injecting the desired immunogen or antigen into a wide variety of vertebrates in accordance with conventional techniques. Suitable vertebrates include mice, rats, rabbits, sheep, and goats, with mice being preferred. Usually, the animals are bled periodically with the successive bleeds having improved titer and specificity. The antigens may be injected intramuscularly, intraperitoneally, subcutaneously, or the like. Chimeric antibodies (mouse human hybrids) made by genetic engineering are also contemplated by this invention.

Polyclonal antibodies are prepared by hyperimmunization of the animal with antigen. Then the blood of the animal is collected shortly after the repeated immunizations and the gamma globulin is isolated. Suitable methods for preparing polyclonal antibodies are described in the *Handbook of Experimental Immunology*, 3d edition, (ed. Weir, 1978), which is herein incorporated by reference.

To obtain monoclonal antibodies, spleen cells from the immunized vertebrate demonstrating the desired antibody response are immortalized. The manner of immortalization is not critical, but the most common method is fusion with a myeloma fusion partner. Other techniques of immortalization include EBV transformation, transformation with bare DNA, such as oncogenes or retroviruses, or any other method which provides for stable maintenance of the cell line and production of monoclonal antibodies. The general process for obtaining monoclonal antibodies is described by Kohler and Milstein, in *Nature,* 256, 495–497 (1975), which is herein incorporated by reference. Human monoclonal antibodies may be obtained by fusion of the spleen cells with an appropriate human fusion partner, such as WI-L2, described in European Application No. 82.301103.6, the relevant portions of which are herein incorporated by reference. A detailed technique for producing mouse x mouse monoclonal antibodies is taught by Oi and Herzenberg, in *Selected Methods in Cellular Immunology,* 351–372 (eds. Mishell and Shiigi, 1980), which also is herein incorporated by reference. The resulting hybridomas are screened to isolate individual clones, each of which secretes a single antibody species capable of recognizing the antigen.

The peptides and/or antibodies may be used without modification or may be modified in a variety of ways, for example, by labeling. Labeling is intended to mean Joining, either covalently or non-covalently, a moiety which directly or indirectly provides for a means of detection. A wide variety of labels are known and include: radionuclides, enzymes, substrates, cofactors, inhibitors, fluorescers, chemiluminescers, magnetic particles, and the like.

Many of the techniques for linking the peptides to suitable labels involve the use of their carboxyl groups, through the use of carbodiimide or active esters to form peptide bonds; the formation of sulfides by reaction of a mercapto group with an activated halogen, such as chloromethylstyrene or activated olefin, such as maleimide; formation of a secondary amine by reaction of an amino group with a dialdelyde such as glutaraldehyde, or the like, followed by reduction with sodium cyanoborohydride, or the like.

The peptides and antibodies of this invention may be used in the preparation of diagnostic tests, such as immunoassays. Such diagnostic techniques include, for example, enzyme immune assay (EIA), enzyme multiplied immunoassay technique (EMIT), enzyme-linked immunosorbent assay (ELISA), radioimmune assay (RIA), fluorescence immune assay, either single or double antibody techniques, and other techniques where either the peptides or antibodies of this invention are labeled with some detectable tag. See generally *Enzyme Immunoassay*, by Maggio, CRC Press (1981). Preferably the peptides of formula I and antibodies thereto are used to detect neutralizing antibodies to IFN-β and measure levels of IFN-β, respectively.

The peptides of this invention can be used as therapeutic agents against antibody mediated neutralization of IFN-β activity. The peptides of this invention can be used alone in straight chain or cyclic ring form, as a polymer wherein adjacent polypeptide repeating units are bonded together by oxidized cysteine residues, or as a conjugate linked to a carrier.

Therapeutic formulations of the novel peptides or fragments or derivatives may be administered in any conventional dosage formulation. While it is possible for the active ingredient to be administered alone, it is preferable to present it as a pharmaceutical formulation. Formulations comprise at least one active ingredient as defined above together with one or more acceptable carriers thereof and optionally other therapeutic agents. Each carrier must be "acceptable" in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy.

EXAMPLE 1

Peptide Synthesis

Reagents used in peptide synthesis were purchased from the indicated vendors: Boc amino acids, Peninsula Laboratories, Belmont, Calif.; dlisopropylcarbodiimide and 1-hydroxybenzotriazole, Aldrich, Milwaukee, Wis.; carbon-14 labelled amino acids, Amersham.

All peptides were synthesized according to established Merrifield solid phase synthetic procedures (Erickson et al., (1976) *Proteins* 2, pp 256–527 and Stewart et al., (1984) *Solid Phase Peptide Synthesis,* Pierce Chemical Co. Rockford Ill.) using an automated instrument, Model 9500, from Biosearch (San Rafael, Calif.). The first amino acid, i.e., the carboxy terminal residue, was esterified to choloromethylated polystyrene-divinylbenzene copolymer (Bio-Rad, 1% cross-linked, 1.34 milli-equivalents/g) as described previously in Hoeprich and Doolittle (1983) Biochemistry 22, pp 2049. Subsequent amino acids were coupled twice using diisopropylcarbodiimide as a coupling agent. In general, the Boc group was removed by treating the protected peptide resin for 20 min with 45% trifluoroacetic acid in dichloromethane (v/v), followed by two 5 min neutralizations with 5% diisopropylethylamine in dichloromethane (v/v). The resin was washed before and after each deprotection, neutralization and coupling step with appropriate solvents. Boc group removal and completeness of coupling was monitored qualitatively by a ninhydrin color test (Kaiser et al., (1970) Anal. Biochem. 34, pp 595). Carbon-14 containing amino acids, e.g., glycine, were coupled initially through a diisopropylcarbodiimide mediated reaction and secondly by utilizing a preformed 1-hydroxybenzotriazole ester.

All peptides were cleaved from the resin with simultaneous side-chain protecting group removal by exposure to anhydrous hydrogen fluoride for 40 min at 0°–4° C. in the presence of 10% anisole (v/v). After removal of hydrogen fluoride by water aspiration, the resin was washed with anhydrous ethyl ether to remove the anisole. The peptide was washed from the resin with sequential washes of dimethylformamide, 50% dimethylformamide/ 10% acetic acid, 10% acetic acid and distilled water; the combined washings were lyophilized.

Purification of the peptides was accomplished by reverse-phase high performance liquid chromatography (HPLC). Using a preparative column (Whatman, Partisil 10 ODS-3 Magnum 20, 2.2 x 50 cm), the desired peptide was eluted during gradient development of the chromatogram; the elution program ranged from 95% solvent A (0.1% trifluoroacetic acid/5% acetonitrile/water) and 5% solvent B (0.1% trifluoroacetic acid/acetonitrile) to 50% A and 50% B over 65 minutes. A portion of each purified peptide was hydrolyzed in 6.0N HCL (Pierce) at 110° C. for 24 hours and amino acid compositions were determined using a Beckman amino acid analyzer Model 121M.

EXAMPLE 2

Binding of Neutralizing mAb's To Synthetic Peptides From rIFN-β

Using the Geysen technique of peptide synthesis described previously, 157 octapeptides were synthesized in duplicate on polyethylene rods or "pins". Each peptide represents an 8-mer made by moving one amino acid at a time through the sequence of rIFN-β. A solution of 175 μl of each neutralizing mAb at an appropriate dilution was mixed with each of the peptide-pins overnight at 4° C. Each peptide-pin was mixed with goat anti-mouse IgG/ horseradish peroxidase (HRP) conjugate and developed with 1 mM 2,2'-Azino-bis(3-ethylbenzthiazoline-6-sulfonic acid) (ABTS) substrate. Results are shown as vertical lines corresponding to the absorbance obtained in the antibody-binding ELISA, plotted above the number of the N-terminal amino acid of each 8-mer peptide within the sequence rIFN-β. This plot shows a peak of binding to amino acids at approximately 40 to 47. (See FIG. 1).

EXAMPLE 3

Reaction of Neutralizing and Non-Neutralizing mAb's With Synthetic Peptides IB, IC and IE.

A series of enzyme-linked immunosorbent assays (ELISA) were run in which a panel of three neutralizing mAb's, identified as A1, A5 and A7 (developed by Phil Redlich and Sid Grossberg at the Medical College of Wisconsin) and a single non-neutralizing mAb, identified as B2b (received from Medical College of Wisconsin, P. Redlich and S. Grossberg), was assessed for binding to synthetic peptides IB, IC, IE, and a control. In each case, the peptide was dissolved in 0.05M Tris buffer, pH 9.5 and aliquoted in 100 μl volumes to wells of a microtiter plate (Corning) at a concentration of 50 μg peptide per well. The plate was placed in a vacuum dessicator overnight to dry the peptide to the well. Standard ELISA procedures were followed after the overnight coupling, i.e. common blocking steps, washes, incubation conditions and color development of the appropriate goat anti-mouse/horseradish peroxidase conjugate with ABTS substrate. MAb A1 reacted well with peptides IB and IC, and to a lesser extent with IE. MAb A5 reacted weakly with all peptides tested. A7 reacted well with peptides IB and IC but virtually no activity was seen with peptide IE. The non neutralizing mAb B2b reacted with peptides IB and IC but not with IE. In all cases, the mAb's irrespective of neutralizing or non-neutralizing activity reacted poorly with a control peptide of comparable size and composition but unrelated to IFN-β. While all mAb's tested bound the synthetic peptides, the neutralizing mAb's showed preferential binding, especially A1 to peptide IB and IC and A5 to peptide IE.

EXAMPLE 4

Inhibition By Synthetic Peptides of Neutralizing mAb Binding to IFN-β

FIG. 6 shows the result of an ELISA wherein the binding of neutralizing mAb's A1, A5 and A7 to IFN-β is significantly inhibited by preincubation with synthetic peptides IB and IC. The neutralizing mAb's were incubated overnight at 4° C. in PBS/tween with a $10^4$ molar excess of peptide. For comparison, non-neutralizing mAb B2b was treated in an identical manner. Each mAb was used at the same concentration, i.e. 1/5000 dilution from a 0.1 mg/ml stock solution. After overnight incubation with peptide, the mAb/peptide solution was run in an ELISA against IFN-β at a concentration of 50 ng/well. The latter was dried on the surface of the well in vacuo as described previously and the ELISA developed according to standard methodologies. It can be seen from FIG. 6 that neutralizing mAb A1 was completely inhibited from binding to IFN-β by peptide IC and peptide IB inhibited 80% of the binding of mAb A1. Binding of mAb A5 to IFN-β was virtually eliminated by preincubation with either peptide compared to binding in the absence of peptide. Binding of mAb A7 to IFN-β in the presence of peptides IB and IC was reduced by 60%. The non-neutralizing mAb B2b binding to IFN-β was decreased about 20% by pre-incubation with peptides IB and IC respectively.

EXAMPLE 5

Antibodies To Synthetic Peptides IB and IC Bind To IFN-β

Antibodies to peptides IB and IC were raised in rabbits immunized with KLH/peptide conjugates. After an appropriate period of time, bleeds were taken and antiserum containing Ab's to each peptide was obtained. Further purification of each antibody population was obtained by ammonium sulfate fractionation of each antiserum sample. The ammonium sulfate cuts were tested by ELISA for reactivity to IFN-β. FIG. 7 shows that the polyclonal Ab population raised against each peptide recognized their respective immunogen, the other related peptide and IFN-β. Peptide IB seems to be more immunogenic than IC, but Ab's raised against the latter react more strongly with IFN-β. While both antibodies recognize IFN-β well, anti-IC could have greater diagnostic utility for measuring IFN-β levels.

What is claimed is:

1. Peptides having specific binding affinity for IFN-β neutralizing antibodies having the following amino acid sequence:

$$X-AA_1-Pro-Glu-Glu-AA_2-AA_3-Gln-AA_4-Y$$

where X is $NH_2$ or an amino acid sequence up to 10 amino acids long, selected in sequence from the following sequence:

$$Tyr-Cys-Leu-Lys-Asp-Arg-Met-Asn-Phe-Asp-;$$

Y is COOH or an amino acid sequence up to 13 amino acids long, selected in sequence from the following sequence:

$$-Gln-Gln-Phe-Gln-Lys-Glu-Asp-Ala-Ala-Leu-Thr-Ile-Tyr;$$

$AA_1$ is Ile, Phe, Leu, Val, Arg, Tyr, or NorLeu;
$AA_2$ is Ile, Leu, Arg, Val, or NorLeu;
$AA_3$ is Lys, Ile, Leu, Arg, Val, or NorLeu; and
$AA_4$ is Leu, Phe, Tyr, Ile, Val, Arg, or Met.

2. Peptides of claim 1 wherein:
$AA_1$ is Ile, Phe, or Leu;
$AA_2$ is Ile, Leu, or Arg;
$AA_3$ is Lys, Ile, or Leu; and
$AA_4$ is Leu, Phe, or Tyr.

3. The peptides of claim 1 wherein:
$AA_1$ is Ile;
$AA_2$ is Ile;
$AA_3$ is Lys; and
$AA_4$ is Leu.

4. The peptides of claim 1 wherein:
X is $NH_2$ and
Y is Gln-Gln-Phe-Gln-Lys-Glu-Asp-Ala-Ala.

5. The peptides of claim 1 wherein:
X is Leu-Lys-Asp-Arg-Met-Asn-Phe-Asp and
Y is COOH.

6. The peptides of claim 1 wherein:
X is Leu-Lys-Asp-Arg-Met-Asn-Phe-Asp and
Y is Gln-Gln-Phe-Gln-Lys-Glu-Asp-Ala-Ala.

7. A method for detecting the presence of neutralizing antibodies to IFN-β comprising:

A) contacting a sample of body fluid from the host suspected of bearing said neutralizing antibodies with a peptide of the formula:

$$X-AA_1-Pro-Glu-Glu-AA_2-AA_3-Gln-AA_4-Y$$

where X is $NH_2$ or an amino acid sequence up to 10 amino acids long, selected in sequence from the following sequence:

$$Tyr-Cys-Leu-Lys-Asp-Arg-Met-Asn-Phe-Asp-;$$

Y is COOH or an amino acid sequence up to 13 amino acids long, selected in sequence from the following sequence:

$$-Gln-Gln-Phe-Gln-Lys-Glu-Asp-Ala-Ala-Leu-Thr-Ile-Tyr;$$

$AA_1$ is Ile, Phe, Leu, Val, Arg, Tyr, or NorLeu;
$AA_2$ is Ile, Leu, Arg, Val, or NorLeu;
$AA_3$ is Lys, Ile, Leu, Arg, Val, or NorLeu; and
$AA_4$ is Leu, Phe, Tyr, Ile, Val, Arg or Met; and B) determining the level of binding of said peptide to said neutralizing antibodies contained in said body fluid as being diagnostic of the presence of IFN-β neutralizing antibodies in said host.

8. The method according to claim 7, wherein:
AA$_1$ is Ile;
AA$_2$ is Ile;
AA$_3$ is Lys; and
AA$_4$ is Leu.

9. The method according to claim 7, wherein:
X is NH$_2$ and
Y is Gln-Gln-Phe-Gln-Lys-Glu-Asp-Ala-Ala.

10. The method of claim 7 wherein:
X is Leu-Lys-Asp-Arg-Met-Asn-Phe-Asp and
Y is COOH.

11. The method of claim 7 wherein:
X is Leu-Lys-Asp-Arg-Met-Asn-Phe-Asp and
Y is Gln-Gln-Phe-Gln-Lys-Glu-Asp-Ala-Ala.

12. A method for reducing the neutralization of IFN-β activity comprising administering to a host an amount of a peptide of claim 1, wherein the amount of the peptide is effective in reducing said neutralization.

13. A method for preventing neutralization of IFN-β activity comprising administering to a host an amount of a peptide of claim 3, wherein the amount of the peptide is effective in reducing said neutralization.

14. A method for treating a person having reduced levels of active IFN-β due to an immune response thereto comprising administering a therapeutically effective amount of a peptide of claim 1.

15. A method for treating a person having reduced levels of active IFN-β due to an immune response thereto comprising administering a therapeutically effective amount of a peptide of claim 3.

16. A method for treating a person having reduced levels of active IFN-β due to an immune response thereto comprising administering a therapeutically effective amount of a peptide of claim 4.

17. A method for treating a person having reduced levels of active IFN-β due to an immune response thereto comprising administering a therapeutically effective amount of a peptide of claim 5.

18. A method for treating a person having reduced levels of active IFN-β due to an immune response thereto comprising administering a therapeutically effective amount of a peptide of claim 6.

19. A diagnostic kit comprising:
A) a peptide having specific binding affinity for IFN-β neutralizing antibodies and having the following amino acid sequence:

$$X-AA_1-Pro-Glu-Glu-AA_2-AA_3-Gln-AA_4-Y$$

where X is NH$_2$ or an amino acid sequence up to 10 amino acids long, selected in sequence from the following sequence:

$$Tyr-Cys-Leu-Lys-Asp-Arg-Met-Asn-Phe-Asp-;$$

Y is COOH or an amino acid sequence up to 13 amino acids long, selected in sequence from the following sequence:

$$-Gln-Gln-Phe-Gln-Lys-Glu-Asp-Ala-Ala-Leu-Thr-Ile-Tyr;$$

AA$_1$ is Ile, Phe, Leu, Val, Arg, Tyr, or NorLeu;
AA$_2$ is Ile, Leu, Arg, Val, or NorLeu;
AA$_3$ Is Lys, Ile, Leu, Arg, Val, or NorLeu; and
AA$_4$ is Leu, Phe, Tyr, Ile, Val, Arg, or Met; and
B) at least one immunoreaction detection reagent.

20. The method of claim 7 wherein:
AA$_1$ is Ile, Phe, or Leu;
AA$_2$ is Ile, Leu, or Arg;
AA$_3$ is Lys, Ile, or Leu; and
AA$_4$ is Leu, Phe, or Tyr.

* * * * *